United States Patent

Watanuki et al.

[11] Patent Number: 5,241,095
[45] Date of Patent: Aug. 31, 1993

[54] METHOD FOR THE PREPARATION OF AN OXIMESILANE COMPOUND

[75] Inventors: Isao Watanuki; Hiroshi Tsumura, both of Gunma; Kazushi Satoh, Tokyo; Nobuhiko Kodana, Gunma, all of Japan

[73] Assignee: Shin-Etsu Chemical Co., Ltd., Tokyo, Japan

[21] Appl. No.: 976,043

[22] Filed: Nov. 13, 1992

[30] Foreign Application Priority Data

Nov. 13, 1991 [JP] Japan ............... 3-325345

[51] Int. Cl.$^5$ ............................................. C07F 7/10
[52] U.S. Cl. ............................................. 556/422
[58] Field of Search ............................................. 516/422

[56] References Cited

U.S. PATENT DOCUMENTS

| 4,033,991 | 7/1977 | Shinohara et al. | 556/422 X |
| 4,126,630 | 11/1978 | Müller et al. | 556/422 X |
| 4,380,660 | 4/1983 | Mathew et al. | 556/422 |
| 4,384,131 | 5/1983 | Kammer et al. | 556/422 |
| 4,705,878 | 11/1987 | Gornowicz et al. | 556/422 |
| 4,918,209 | 4/1990 | Baule et al. | 556/422 |
| 4,990,642 | 2/1991 | Häring | 556/422 |
| 5,087,718 | 2/1992 | Zoche | 556/422 |
| 5,171,872 | 12/1992 | Watanuki et al. | 556/422 |

FOREIGN PATENT DOCUMENTS 0293306  11/1988  European Pat. Off.
4041649  6/1992  Fed. Rep. of Germany.

Primary Examiner—Paul F. Shaver
Attorney, Agent, or Firm—Millen, White, Zelano & Branigan

[57] ABSTRACT

An efficient and safe method is proposed for the preparation of an oximesilane compound having a group of the general formula —O—N=CR$^2$R$^3$, in which R$^2$ and R$^3$ are each a hydrogen atom or a monovalent hydrocarbon group, bonded to the silicon atom. The method consists of successive steps of which the first is for the reaction of a chlorosilane compound with ammonia and the second is for the reaction of the reaction mixture coming from the first step with an oxime compound to introduce the oxime groups as bonded to the silicon atom. Different from conventional methods in which formation of an explosive compound such as hydrochloride of an organic base or oxime compound is unavoidable, the inventive method does not involve formation of such an explosive by-product so that the desired oximesilane compound can be obtained without the danger of explosion.

9 Claims, 1 Drawing Sheet

FIGURE
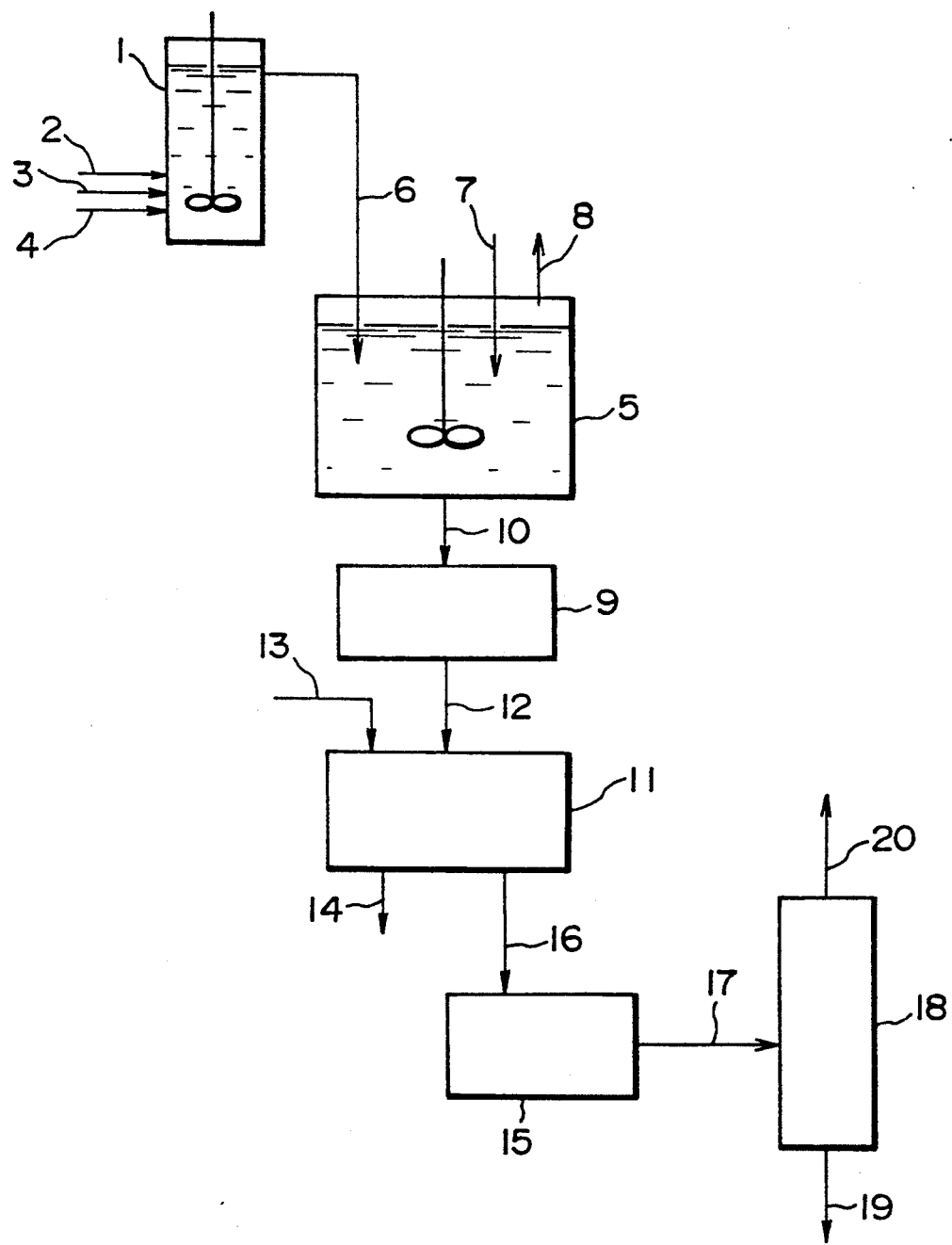

METHOD FOR THE PREPARATION OF AN OXIMESILANE COMPOUND

BACKGROUND OF THE INVENTION

The present invention relates to a method for the preparation of an oximesilane compound. More particularly, the invention relates to an efficient method for the preparation of an oximesilane compound without the risk of forming an oxime hydrochloride having explosiveness and unavoidably formed in the prior art methods.

An oximesilane compound, such as methyl tris(methyl ethyl ketoxime) silane of the formula MeSi(—O—N=CMeEt)$_3$ and vinyl tris(methyl ethyl ketoxime) silane of the formula ViSi(—O—N=CMeEt)$_3$, in which Me is a methyl group, Et is an ethyl group and Vi is a vinyl group, is a useful organosilicon compound to serve, for example, as a crosslinking agent in certain types of room temperature-curable organopolysiloxane rubber compositions. These oximesilane compounds are prepared in the prior art by the method disclosed, for example, in Japanese Patent Publication 39-29837, according to which a chlorosilane compound such as methyl trichlorosilane MeSiCl$_3$ is subjected to a dehydrochlorination reaction with an at least stoichiometrically equivalent amount of an oxime compound such as methyl ethyl ketoxime of the formula MeEtC=N—OH in the presence of an excess amount of an organic base such as pyridine as an acceptor of the hydrogen chloride produced by the dehydrochlorination reaction. A problem in this method is that, while it is necessary to isolate the desired oximesilane compound from the hydrochloride of the organic base, e.g., pyridine hydrochloride, by distillation, hydrochlorides of an organic base are sometimes explosive to cause serious explosion during the distillation procedure.

It is also proposed in Japanese Patent Publication 1-21834 that the dehydrochlorination of a chlorosilane compound for the preparation of an oximesilane compound is performed in the presence of an oxime compound in an amount twice as large as the stoichiometrically equivalent amount and the excess of the oxime compound serves as an acceptor of the hydrogen chloride so that addition of a separate organic base compound is not required. This method is also not free from the danger of explosion during processing of the reaction mixture since hydrochlorides of an oxime compound are generally explosive. In addition, oxime compounds are generally expensive so that the hydrochloride thereof cannot be discarded as such necessitating facilities for the recovery and recycling of the oxime compound from the hydrochloride thereof.

It is further proposed in Japanese Patent Kokai 63-227592 that the dehydrochlorination of a chlorosilane compound and an oxime compound is performed while ammonia gas is blown into the reaction mixture to serve as an acceptor of the hydrogen chloride so that an oximesilane compound can be prepared in a continuous process. A problem in this method is that the reaction must be performed under control of the temperature of the reaction mixture by using a non-inflammable halogenated hydrocarbon solvent such as perchloro fluorinated alkanes, trichlorotrifluoroethanes and the like, most of which are industrially banned due to the problem in the environmental pollution.

SUMMARY OF THE INVENTION

The present invention accordingly has an object to provide a novel and efficient method for the preparation of an oximesilane compound from a halogenosilane compound as the starting material without the above described disadvantages in the prior art methods, in particular, relative to the danger of explosion.

Thus, the method of the present invention for the preparation of an oximesilane compound represented by the general formula $$R^1{}_{4-n}Si(-O-N=CR^2R^3)_n, \quad (I)$$

in which $R^1$ is an unsubstituted or substituted monovalent hydrocarbon group, $R^2$ and $R^3$ are each, independently from the other, a hydrogen atom or an unsubstituted or substituted monovalent hydrocarbon group and the subscript n is 1, 2, 3 or 4, comprises the steps of:

(a) introducing continuously a halogenosilane compound represented by the general formula $$R^1{}_{4-n}SiX_n, \quad (II)$$

in which $R^1$ and n each have the same meaning as defined above and X is an atom of halogen, into a first reaction zone together with ammonia in a molar proportion of ammonia in the range from 1.55n to 2.1n moles per mole of the halogenosilane compound, precipitates of an ammonium halide being formed in the reaction mixture;

(b) introducing the reaction mixture containing the precipitates of the ammonium halide continuously withdrawn from the first reaction zone into a second reaction zone together with an oxime compound represented by the general formula $$R^2R^3C=N-OH, \quad (III)$$

in which $R^2$ and $R^3$ each have the same meaning as defined above, in a molar proportion of the oxime compound in the range from 1.0n to 1.1n moles per mole of the halogenosilane compound introduced into the first reaction zone to form an oximesilane compound by the reaction therebetween;

(c) continuously withdrawing the reaction mixture containing the precipitates of the ammonium halide from the second reaction zone; and (d) removing the precipitates of the ammonium halide from the reaction mixture.

BRIEF DESCRIPTION OF THE DRAWING

The FIGURE is a schematic block diagram of a typical apparatus system to perform the inventive method in a semi-continuous process.

DETAILED DESCRIPTION OF THE PREFERRED EMBODIMENTS

As is described above, the inventive method comprises the four steps, of which the first step, i.e. step (a), is for the reaction of a starting halogenosilane compound of the general formula (II) with ammonia in a first reaction zone and the second step, i.e. step (b), is for the reaction of the reaction mixture withdrawn from the first reaction zone with an oxime compound of the general formula (III) to form the desired oximesilane compound represented by the above given general formula (I). The steps (c) and (d) are for the isolation of the oximesilane compound from the reaction mixture in the second reaction zone.

The starting material used in the inventive method is a halogenosilane compound represented by the above given general formula (II). In the formula, $R^1$ is an unsubstituted or substituted monovalent hydrocarbon group exemplified by alkyl groups such as methyl, ethyl, propyl and butyl groups, cycloalkyl groups such as cyclohexyl group, alkenyl groups such as vinyl, allyl and butenyl groups and aryl groups such as phenyl and tolyl groups as well as those substituted groups obtained by replacing a part or all of the hydrogen atoms in the above named hydrocarbon groups with halogen atoms such as chloromethyl and 3,3,3-trifluoropropyl groups. The symbol X denotes an atom of halogen which is preferably chlorine or fluorine or, more preferably, chlorine. The subscript n is 1, 2, 3 or 4.

Particular examples of the halogenosilane compounds to which the inventive method is applicable include tetrachlorosilane, trimethyl chlorosilane, dimethyl dichlorosilane, methyl trichlorosilane, methyl ethyl dichlorosilane, ethyl trichlorosilane, diethyl dichlorosilane, triethyl chlorosilane, n-propyl trichlorosilane, isopropyl trichlorosilane, 2-chloroethyl trichlorosilane, 3-chloropropyl trichlorosilane, triethyl chlorosilane, vinyl trichlorosilane, vinyl mehyl dichlorosilane, isopropenyl trichlorosilane, allyl trichlorosilane, phenyl trichlorosilane, benzyl trichlorosilane and the like, of which those in which the group $R^1$ is a methyl or vinyl group and the subscript n is 3 are most frequently used in the inventive method in view of the usefulness of the oximesilane compounds derived therefrom.

The nature of the reaction taking place between the above defined halogenosilane compound and ammonia gas in step (a) of the inventive method is not well analyzed but it is presumable that the silicon-bonded halogen atoms are replaced with amino groups of the formula —$NH_2$ or a silazane linkage $\equiv Si-NH-Si\equiv$ is formed between the silicon atoms with formation of an ammonium halide as the by-product.

In carrying out the step (a), the halogenosilane compound and ammonia are continuously introduced into a first reaction zone. It is preferable that an organic solvent is also introduced into the first reaction zone separately or together with the halogenosilane compound with an object to ensure smooth proceeding of the reaction and decrease the consistency of the reaction mixture after the reaction in the first reaction zone which is in the form of a slurry containing the precipitates of the ammonium halide. Suitable organic solvents include toluene, hexane, petroleum ether and the like though not particularly limitative thereto. The rate of introduction of the ammonia into the first reaction zone should be such that from 1.55 n to 2.1 n moles or, preferably, from 1.60 n to 1.95 n moles of ammonia are introduced per mole of the halogenosilane compound. The rate of introduction of the organic solvent, when used, is preferably in the range from 1 to 20 times by weight relative to the halogenosilane compound.

Though not critical, the above described reaction of the halogenosilane compound and ammonia is performed at room temperature or at a temperature in the range from 0° to 100° C. or, preferably, in the range from 25° to 70° C. but not to cause boiling of the reaction mixture. Needless to say, the reaction velocity can be increased as the temperature is increased although the reaction product would eventually be colored when the temperature is too high. Since the reaction proceeds exothermically, the reaction is performed in a reaction vessel equipped with a stirrer and provided with a cooling means such as a jacket for cooling water. It is preferable to use a vertical reactor and the halogenosilane compound, ammonia and organic solvent are introduced into the reactor at the bottom thereof and the reaction mixture is discharged from the top of the reactor. The staying time of the reaction mixture in the first reaction zone in such a vertical reactor is in the range from 0.5 to 10 minutes or, preferably, from 1 to 5 minutes.

The reaction mixture discharged out of the first reaction zone in the above described manner is then introduced in step (b) of the inventive method into a second reaction zone where it is reacted with an oxime silane compound concurrently introduced thereinto. The oxime compound is represented by the general formula (III) given before, in which $R^2$ and $R^3$ are each, independently from the other, a hydrogen atom or an unsubstituted or substituted monovalent hydrocarbon group depending on the kind of the desired oximesilane compound as the final product. The monovalent hydrocarbon groups denoted by $R^2$ and $R^3$ can be methyl, ethyl, propyl, butyl, pentyl, hexyl, vinyl, butenyl, cyclopentyl, cyclohexyl, cyclooctyl, 3-methyl-1-hexenyl, cyclopentenyl, phenyl and tolyl groups though not particularly limitative thereto.

Particular examples of the oxime compounds to which the inventive method is applicable include, though not particularly limitative, formaldoxime, acetaldoxime, acetone oxime, methyl ethyl ketoxime, diethyl ketoxime, cyclohexanoxime, 4-methylcyclohexanoxime, 4-chlorocyclohexanoxime, acetophenoxime, benzophenoxime, benzyl ethyl ketoxime, methyl cyclohexyl ketoxime, benzaldoxime and the like, of which formaldoxime, acetaldoxime, acetone oxime, methyl ethyl ketoxime, diethyl ketoxime and cyclohexanoxime are important and methyl ethyl ketoxime and acetone oxime are more important in respect of the usefulness of the oximesilane compounds derived therefrom.

The rate of introduction of the oxime compound into the second reaction zone is preferably in the range from 1.0 n to 1.1 n moles or, more preferably, from 1.01 n to 1.06 n moles per mole of the halogenosilane compound introduced into the first reaction zone in step (a) since the reaction proceeds almost quantitatively. The second reaction zone is kept at a temperature in the range from 0° to 100° C. or, preferably, from 25° to 75° C. The reaction vessel in which the second reaction zone is formed is not required to be provided with a cooling means such as a jacket for cooling water since the reaction proceeding in this second reaction zone is not so highly exothermic as in the reaction of the step (a). The staying time of the reaction mixture in the second reaction zone is in the range from 5 to 60 minutes or, preferably, from 10 to 40 minutes although it is important to select the exact staying time in consideration of various factors such as the kinds of the reactants, kind and amount of the organic solvent, reaction temperature and so on.

The reaction taking place in the second reaction zone between the reaction mixture coming from the first reaction zone and the oxime compound, which is introduced into the reaction vessel preferably through an in-liquid dropping tube, in step (b) of the inventive method is a replacement reaction of the Si—$NH_2$ linkage with the Si—(—O—N=$CR^2R^3$) linkage producing ammonia as a by-product of the reaction. The ammonia thus produced would react with any trace amount of the unreacted halogenosilane compound remaining in the reaction mixture coming from the first reaction zone so as to prevent formation of an oxime salt of a halogen-containing acid along with the effect of preventing coloration of the desired oximesilane compound by the halogenosilane compound. It is a preferable process that the ammonia produced in the second reaction zone is introduced into and absorbed by the organic solvent to be introduced into the first reaction zone.

The oximesilane compound as the desired product is isolated from the reaction mixture after step (b) in a conventional procedure. Namely, the reaction mixture containing the precipitates of ammonium halide and continuously discharged out of the second reaction zone is first filtered to remove the precipitates and the filtrate is subjected to distillation to recover the organic solvent and the unreacted oximesilane compound, if any. It is important that the temperature of the reaction mixture in the distillation does not exceed 90° C. because the product oximesilane compound is sometimes colored when the temperature of the distillation is too high. In this regard, the distillation is performed preferably under reduced pressure.

Following is a brief description of the inventive method making reference to the accompanying drawing. The figure in the accompanying drawing illustrates a schematic block diagram of the typical apparatus system to perform the inventive method in a semi-continuous process. In this reaction system, the starting halogenosilane compound and the organic solvent are continuously introduced into the vertical reactor column 1, which is equipped with a stirrer and provided with a jacket for cooling water, at the bottom thereof through the lines 2 and 3, respectively, while ammonia gas is introduced also continuously into the reactor column 1 at the bottom through the line 4 simultaneously as the silane compound and solvent. The reaction between the halogenosilane and ammonia proceeds while the reaction mixture ascends from the bottom to the top of the vertical reactor column 1 with a staying time of 1 to 5 minutes. The space inside the reactor column 1 above the liquid phase is filled with a dry inert gas to ensure an anhydrous condition.

The reaction mixture containing the precipitates of ammonium halide after the reaction in the vertical reactor column 1 is discharged out of the reactor column 1 through the line 6 and introduced into the reaction vessel 5 for the second reaction zone to effect the reaction with an oxime compound. The oxime compound to be reacted with the reaction mixture coming from the reactor column 1 is introduced into the reaction vessel 5 through the line 7 concurrently with introduction of the reaction mixture thereinto. As is mentioned before, ammonia is produced as a by-product in the reaction taking place in this reaction vessel 5 and discharged out of the line 8. The ammonia gas can be recycled to the first reaction zone.

After completion of the reaction in the second reaction zone, the reaction mixture containing the precipitates of ammonium halide in the reaction vessel 5 is discharged through the line 10 and introduced into the slurry reservoir 9 from which it is transferred through the duct 12 to the filtering machine 11 where it is filtered and, if necessary, the cake is washed with an organic solvent coming through the line 13. The cake of the ammonium halide is discharged from the filtering machine 11 through the line 14 while the filtrate is introduced through the line 16 into the reservoir 15. The filtrate in the reservoir 15 is sent through the line 17 to the stripping column 18 where the filtrate is stripped under reduced pressure to be freed from the organic solvent and other volatile matters contained therein as the distillate discharged from the line 20 while the oximesilane compound as the desired product is obtained from the line 19.

In the following, the method of the present invention is described in more detail by way of examples.

EXAMPLE 1

Into a reactor column having an inner diameter of 80 mm and a height of 110 mm equipped with a Teflon-made stirrer and provided with a jacket for cooling water were continuously introduced vinyl trichlorosilane and toluene at the bottom of the column at rates of 934 g/hour and 5887 g/hour, respectively, with concurrent introduction of ammonia gas at a constant rate of 700 liters (N.T.P.)/hour. The rate of introduction of ammonia gas corresponded to 5.4 moles per mole of the silane compound. The reaction mixture in the reactor column was kept at a temperature of 60° to 75° C. The staying time of the reaction mixture in the reactor column was 4 minutes.

The reaction mixture discharged from the reactor column at the top thereof was introduced into a Teflon-made reaction vessel of 10 liters capacity along with concurrent introduction of methyl ethyl ketoxime at a rate of 1555 g/hour corresponding to a rate of 3.09 moles per mole of the silane compound introduced into the reactor column. The staying time of the reaction mixture, which was kept at a temperature of 60° to 65° C., in the reaction vessel was 40 minutes.

The reaction mixture discharged out of the reaction vessel was introduced into a slurry reservoir and collected over 5 hours of the reaction continued in the above described manner. The reaction mixture was transferred into a pressurizable filtering machine and freed from the precipitates of ammonium chloride. The filtrate was subjected to stripping of volatile matters at 75° to 80° C. under a pressure of 30 mmHg or below. The residual liquid in the stripper still was gas chromatographically analyzed to find that the principal constituent thereof was vinyl tris(methyl ethyl ketoxime) silane and the purity thereof was 95.1%. The yield of this product was 93% of the theoretical value taking the amount of the vinyl trichlorosilane as the base.

EXAMPLE 2

The experimental procedure was substantially the same as in Example 1 excepting modification of the rates of introduction of the reactants and solvent into the respective reactors which were the same as used in Example 1. Namely, vinyl trichlorosilane, toluene and ammonia gas were introduced into the reactor column at rates of 1870 g/hour, 9350 g/hour and 1268 liters (N.T.P.)/hour, respectively, while methyl ethyl ketoxime was introduced into the reaction vessel at a rate of 3173 g/hour. The rates of introduction of the ammonia gas and the oxime compound corresponded to 4.89 moles and 3.15 moles, respectively, per mole of the silane compound. The staying times of the reaction mixture in the first and the second reaction zones were 2.4 minutes and 20 minutes, respectively. The yield of vinyl tris(methyl ethyl ketoxime) silane as the product was 91% of the theoretical value taking the amount of the vinyl trichlorosilane as the base.

EXAMPLE 3

The experimental procedure was substantially the same as in Example 1 excepting replacement of vinyl trichlorosilane as the starting reactant with methyl trichlorosilane and modification of the rates of introduction of the reactants and solvent into the respective reactors which were the same as used in Example 1. Namely, methyl trichlorosilane, toluene and ammonia gas were introduced into the reactor column at rates of 1313 g/hour, 6171 g/hour and 1091 liters (N.T.P.)/hour, respectively, while methyl ethyl ketoxime was introduced into the reaction vessel at a rate of 2337 g/hour. The rates of introduction of the ammonia gas and the oxime compound corresponded to 5.55 moles and 3.06 moles, respectively, per mole of the silane compound. The staying times of the reaction mixture in the first and the second reaction zones were 3.6 minutes and 34 minutes, respectively. The yield of methyl tris(methyl ethyl ketoxime) silane as the product was 94% of the theoretical value taking the amount of the methyl trichlorosilane as the base.

What is claimed is:

1. A method for the preparation of an oximesilane compound represented by the general formula $$R^1{}_{4-n}Si(-O-N=CR^2R^3)_n,$$

in which $R^1$ is an unsubstituted or substituted monovalent hydrocarbon group, $R^2$ and $R^3$ are each, independently from the other, a hydrogen atom or an unsubstituted or substituted monovalent hydrocarbon group and the subscript n is 1, 2, 3 or 4, which comprises the steps of:

(a) introducing continuously a halogenosilane compound represented by the general formula $$R^1{}_{4-n}SiX_n,$$

in which $R^1$ and n each have the same meaning as defined above and X is an atom of halogen, into a first reaction zone together with ammonia gas in a molar proportion of ammonia in the range from 1.55 n to 2.1 n moles per mole of the halogenosilane compound, precipitates of an ammonium halide being formed in the reaction mixture;

(b) introducing the reaction mixture containing the precipitates of the ammonium halide continuously withdrawn from the first reaction zone into a second reaction zone together with an oxime compound represented by the general formula $$R^2R^3C=N-OH,$$

in which $R^2$ and $R^3$ each have the same meaning as defined above, in a molar proportion of the oxime compound in the range from 1.0 n to 1.1 n moles per mole of the halogenosilane compound introduced into the first reaction zone in step (a) to form an oximesilane compound by the reaction therebetween;

(c) continuously withdrawing the reaction mixture containing the precipitates of the ammonium halide from the second reaction zone; and (d) removing the precipitates of the ammonium halide from the reaction mixture.

2. The method for the preparation of an oximesilane compound as claimed in claim 1 in which the halogen denoted by X in the halogenosilane compound is chlorine.

3. The method for the preparation of an oximesilane compound as claimed in claim 1 in which the amount of the ammonia gas in step (a) is in the range from 1.60 n to 1.95 n moles per mole of the halogenosilane compound.

4. The method for the preparation of an oximesilane compound as claimed in claim 1 in which the reaction of step (a) is performed at a temperature in the range from 25° to 70° C.

5. The method for the preparation of an oximesilane compound as claimed in claim 1 in which the amount of the oxime compound in step (b) is in the range from 1.01 n to 1.06 n moles per mole of the halogenosilane compound.

6. The method for the preparation of an oximesilane compound as claimed in claim 1 in which the reaction of step (b) is performed at a temperature in the range from 25° to 75° C.

7. The method for the preparation of an oximesilane compound as claimed in claim 1 in which the reaction mixture in step (a) is diluted with an organic solvent in an amount in the range from 1 to 20 times by weight based on the halogenosilane compound.

8. The method for the preparation of an oximesilane compound as claimed in claim 1 in which the staying time of the reaction mixture in the first reaction zone in step (a) is in the range from 30 seconds to 10 minutes.

9. The method for the preparation of an oximesilane compound as claimed in claim 1 in which the staying time of the reaction mixture in the second reaction zone in step (b) is in the range from 5 to 60 minutes.

* * * * *